United States Patent
Chen (10) Patent No.: US 7,229,837 B2
(45) Date of Patent: Jun. 12, 2007

(54) ENHANCED PHOTOPHYSICS OF CONJUGATED POLYMERS

(75) Inventor: Liaohai Chen, Darien, IL (US)

(73) Assignee: UChicago Argonne, LLC, Chicago, IL (US)

( * ) Notice: Subject to any disclaimer, the term of this patent is extended or adjusted under 35 U.S.C. 154(b) by 760 days.

(21) Appl. No.: 10/449,287

(22) Filed: May 30, 2003

(65) Prior Publication Data
US 2003/0224525 A1 Dec. 4, 2003

Related U.S. Application Data

(60) Provisional application No. 60/384,757, filed on May 30, 2002.

(51) Int. Cl.
G01N 21/64 (2006.01)
G01N 33/48 (2006.01)

(52) U.S. Cl. ............... 436/172; 436/63; 436/54; 436/164; 422/82.05; 422/82.08; 977/773; 977/788; 977/920; 977/924; 977/927

(58) Field of Classification Search ............... 436/63, 436/64, 164, 172, 174; 422/55, 82.05, 82.08; 525/327.1, 328.1, 332.8, 332.9, 333.2, 359.3; 977/773, 788, 927, 920, 924
See application file for complete search history.

(56) References Cited

U.S. PATENT DOCUMENTS 5,965,281 A * 10/1999 Cao .................. 428/690
6,569,952 B1 * 5/2003 Chen et al. ............... 525/327.1
6,737,279 B1 * 5/2004 Chen .................... 436/546
6,780,379 B1 * 8/2004 Chen et al. ............... 422/82.08

OTHER PUBLICATIONS

J. Kim and M. Swager, Control of Conformational and Interpolymer Effects In Conjugated Polymers, NATURE 411 (6841), 1030-034 (2001).
D. Moses, J. Wang A.J. Heeger, N. Kirova, B. Brazolski, Singlet Exciton Binding Energy In Poly(Phenylene Vinylene), PNAS, Nov. 20, 2001, vol. 98, No. 24.
T.Q. Nguyen, J.Wu, V. Doan, B.J. Schwatz, et al, Control of Energy Transfer in Oriented Conjugated Polymer-Mesoporous Silica Composites, Science, vol. 288, 652-656 (2000).
T. Huser, M. Yan, L. Rothberg, Single Chain Spectroscopy of Conformational Dependence of Conjugated Polymer Photophysics, Proc. Natl. Acad. Sci. 97 (21), 11187-11191 (2000).
H. Sirringhaus et al., Two-Dimensional Charge Transport in Self-Organized High Mobilitgy Conjugated Polymers, Nature 401, 685-688, (1999).
H. L. Wang, D. McBranc et al., Controlled Unidirectional Energy Transfer inLuminescent Self-Assembled Conjugated Polymer Superlattices, Chem. Phys. Lett. 315 (3,4), 173-180, 1999.

(Continued)

*Primary Examiner*—Maureen M. Wallenhorst
(74) *Attorney, Agent, or Firm*—Olson & Hierl, Ltd.; Harry M. Levy (57) ABSTRACT

A particulate fluorescent conjugated polymer surfactant complex and method of making and using same. The particles are between about 15 and about 50 nm and when formed from a lipsome surfactant have a charge density similar to DNA and are strongly absorbed by cancer cells.

26 Claims, 5 Drawing Sheets

OTHER PUBLICATIONS

L. Chen, S. Xu, D. McBranch, D. Whitten, Tuning The Properties of Conjugated Polyelectrolytes through Surfactant Complexation, J. Am. Chem. Soc. 2000, 122, 9302-9303.

L. Chen, D. McBranch, R. Wang, D. Whitten, Surfactant-Induced Modification of Quenching of Conjugated Polymer Fluorescence by Electron Acceptors: Applications for Chemical Sensing, Chemical Physics Letters 330 (2000) 27-33.

L. Chen, D. McBranch, D. Whitten, Super Quenching Behavior Between a Conjugated Polymer and Molecular Quenchers and its Applications in Biological/Chemical Sensors, SPIE Conference on Adv. Mat. and Optical Sys. for Chem. and Biological Detection, Boston, MA., Sep. 1999, SPIE vol. 3858, 32-39.

L. Chen, D.. W. McBranch, H. Wang, R. Helgeson, F. Wudi, D. Whitten, Highly Sensive Biological and Chemical Sensors Based on Reversible Fluorescence Quenching in A Conjugated Polymer, PNAS, Oct. 26, 1999, vo.. 96, No. 22, 12287-12292.

W. J. Macknight, E. A. Ponomarenko, D.A. Tirrell, Self-Assembled Polyelectrolyte-Surfactant Complexes in Nonaqueous Solvents and In the Solid State, vol. 31, No. 12, Accounts of Chemical Research, Dec, 1998.

C.R. Safinya, Structures of Lipid-DNA Complexes: Supramolecular Assembly and Gene Delivery, Current Opinion in Structural Biology 2001, 11: 440-448.

J.O. Radler, I. Koltover, T. Salditt, C.R. Safinya, Structure of DNA-Cationic Lipsome Complexes: DNA Intercalation in Multilamellar Membranes In Distinct Interhelical Packing Regimes, Science, vol. 275, Feb. 7, 1997.

A. Dogariu, A.J. Heeger, H. Wang, Photophysics of poly(2,3-diphenyl-5 -hexyl-p-phenylene vinylene), Physical Review B, vol. 61, No. 23, Jun. 15, 2000-1.

M.G. Colombo, L. Citti, G.Basta, R Decaterina, A. Biagini, G. Rainaldi, Differential Ability of Human Endothelial Cells in Internalize and Express Exogenous DNA, Cardiovascular Drugs and Therapy, 15 25-29, 2001.

M. Teifel, L. Heine, S. Milbredt, P. Friedl, Optimization of Transfection of Human Endothelial Cells, Endothelium, vol. 5, pp. 21-35, 1997.

* cited by examiner

ENHANCED PHOTOPHYSICS OF CONJUGATED POLYMERS

RELATED APPLICATIONS

This application, pursuant to 37 C.F.R. 1.78(c), claims priority based on provisional application Ser. No. 60/384,757 filed on May 30, 2002.

CONTRACTUAL ORIGIN OF THE INVENTION

The United States Government has rights in this invention pursuant to Contract No. W-31-109-ENG-38 between the U.S. Department of Energy (DOE) and The University of Chicago representing Argonne National Laboratory.

FIELD OF THE INVENTION

The present invention relates generally to ionic conjugated polymers. More specifically, the present invention applies to fluorescent ionic conjugated polymers complexed with oppositely charged surfactants to form nano-sized particles of a polymer-surfactant complex some of which have similar charge densities as DNA characterized by enhanced photophysical properties and to methods of producing and using the same.

BACKGROUND OF THE INVENTION

Polymers enjoy an expanding range of application. Conjugated polymers have been widely recognized for their potential as inexpensive and versatile electronic materials for many applications. Because of their wide-ranging applicability, major efforts have been focused on determining the relationship between the polymer chemical structure and conformation and the corresponding physical and chemical properties of polymer materials. Common efforts have focused on altering polymer properties by modifying the polymer conformation through changes in the polymer/monomer design and through synthesis steps that change the conjugated repeat units of the polymer.

For example, the fluorescence emission wavelength may be tuned over the entire visible range to obtain variable-color LEDs by varying polymer substituent groups to tune the π-electron density. The fluorescence can be further tuned over an additional 100 nm by varying the repeat unit to construct polymers with varying degrees of rigidity. These methods also affect the conductivity and quantum efficiency of fluorescent polymers. One of the most challenging aspects of these prior art methods is that a polymer's properties are altered by changing the repeat unit conformation of that polymer. This means that a new polymer must be synthesized for each desired variation of the polymer's electronic or photophysical properties.

Prior work of mine and others at Los Alamos National Laboratory related to polymer-surfactant complexes exhibiting many other improved photophysical properties; the properties and the degree of improvement may vary depending on the polymer and surfactant used to form the complex. These complexes may exhibit flourescence quantum efficiency improvement by a factor ranging from 2 to 20, or more, when compared to the next polymer. Complexes according to my prior work may have emission spectra that are excitation wavelength independent. They may have absorption spectra that are narrowed and red-shifted when compared to the neat polymer. The fluorescence of the polymer-surfactant complexes may also be characterized by single exponential decay kinetics rather than the less stable, multi-exponential decay characteristics of neat polymers. The polymer-surfactant complexes of my prior work were very important, but one area in which they were lacking was in well defined solid state materials. When dried, the previous polymer surfactant materials resulted in large agglomerates, many of which lost important physical properties during precipitation. Moreover, the precipitants as large agglomerates are not as useful as smaller particles.

SUMMARY OF THE INVENTION

Accordingly, an object of the invention is to provide nano-sized particles using the complexing interaction of conjugated polymers and selected surfactants.

Another object of the invention is to provide nano-sized particles as hereinbefore set forth in which enhanced photophysical properties such as emission efficiency is provided in the solid state phase.

Another object of the present invention is to provide nano-sized particles as hereinbefore set forth in which the emission spectrum is dependent upon and controlled by particle sized distribution;

Another object of the present invention is to provide nano-sized particles as hereinbefore set forth which are easily insertable into cells, particularly cancer cells to provide indicators of the presence thereof.

Yet another object of the present invention is to provide a particulate fluorescent conjugated polymer-surfactant particulate composition comprising: an ionic conjugated polymer having fluorescent properties complexed with an oppositely charged surfactant, wherein the complex is characterized by at least one enhanced photophysical property and the particles have an average diameter less than about (50) nm.

A still further object of the present invention is to provide a particulate fluorescent conjugated polymer-surfactant composition comprising a polyanionic derivative of polyphenylene vinylene having fluorescent properties complexed with a cationic liposome surfactant, wherein the complex is characterized by at least one enhanced photophysical property and the particles have an average diameter less than about (50) nm.

Yet another object of the present invention is to provide a method of preparing a particulate fluorescent conjugated polymer-surfactant composition having average diameters of less than about 50 nanometers comprising: providing a solution comprising an ionic conjugated polymer having fluorescent properties in polar solvent; combining an effective amount of oppositely charged sonicated surfactant capable of forming a bilayer structure with the polymer solution to form polymer-surfactant complex particulates wherein the particulates exhibit at least one enhanced photophysical property compared to the neat polymer and have average diameters of less than about 50 nanometers.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DETAILED DESCRIPTION OF THE PREFERRED EMBODIMENT

The present invention is based on the discovery that combining certain fluorescent ionic conjugated polymers with certain oppositely charged surfactants produces nano-sized particles complexes with at least one enhanced photophysical property. Fluorescent polymers are used in many applications, and they have become very important in medical and biological research. Applications for fluorescent polymers demand high stability, tunability and high fluorescence efficiencies. The present invention discloses solid state phase nano-sized particles of complexes that provide these features and methods for producing and using the complexes.

Fluorescent ionic conjugated polymers combined with oppositely charged surfactants form a complex described herein as a polymer-surfactant complex. Particulates of these complexes may be formed in solution with the solution typically including one or more inert polar solvents. The ionic conjugated polymer and the surfactant are preferably soluble in and chemically compatible with the solvent. Though a surfactant is commonly added to a polymer solution, a polymer may be added to a surfactant solution. Water is a presently preferred polar solvent. Other polar solvents may also be used, including, but not limited to tetrahydrofuran (THF), dioxane, N,N-dimethylformamide (DMF), N,N-dimethylacetamide (DMAC), N-methylpyrrolidone (NMP), dimethylsulfoxide (DMSO), acetone, or a lower alkyl alcohol ($C_1$ to $C_4$). Mixtures of solvents may be used.

The polymer used to form the polymer-surfactant complex may be any ionic conjugated polymer or polyelectrolyte having fluorescent properties. Many ionic conjugated polymers have fluorescent properties, including, but not limited to, substituted and unsubstituted forms of poly(phenylene vinylene), poly (silyl-phenylene vinylene), poly (thienylene vinylene), poly(napththalene vinylene), poly (quinoline vinylene), poly(pyridine vinylene), poly(fluorene), poly (thiophene), and derivatives thereof. The polymer will typically have an ionic side chain or ionic moieties that interact with the oppositely charged surfactant. The surfactant used in the present invention may be any oppositely charged liposome surfactant, which complexes with the polymer to form nano-particles having average particle diameters in the range of from about 15 to about 50 nanometers.

Surfactant molecules that can be used to form ionic conjugated polymer based particles are ones which form a bilayer structure, such as liposome molecule having an opposite charge to the ionic conjugated polymer. One particle example for such a surfactant molecule is N-[1-(2,3-Dioleoyloxy)propyl]-N,N,N,-trimethylammonium chloride, ($C_{43}H_{83}NO_8S$, MW:774,21) (DOTAP).

In one example of nano-sized particles, 1.4 mg of DOTAP was dissolved in 100 ml water (or phosphate buffered saline (PBS)), and probe-sonicated (Model W-220F, Heat System-Ultrasonics, Inc. Plainview, N.Y.) for 3 minutes. The solution was then slowly mixed with $2 \times 10^{-5}$ M [poly(2,5-methoxy propyloxy sulfonate phenylene vinylene) (MPS-PP V] water (or PBS buffer) solution (repeat-unit concentration) at the mole-ratio of 1:1. The mixture was again probe sonicated for 2 minutes while the temperature was maintained by immersing the solution under the ice-water bath. The solution was then filtered with a 0.1 μm pore-size syringe filter. A clear solution which contained DOTAP-MPS-PPV particles was obtained. To obtain smaller size particles, the above solution was filtered with a 20 nm pore-size filter (Whatman Anodisc 13) using a size extruder. The resulted solution was then concentrated to a half of its volume using a centrivap concentrator (Labconco). Particles formed at ratios of surfactant to polymers ranging from 0.5:1 to 2:1.

The full linear length of MPS-PP backbone is in the order of a micrometer. In order to create nano-sized conjugated polymer-based particles. I folded the polymer chain in nanometer scale in a controllable fashion. This was achieved by further exploiting the interaction of MPS-PPV with selected surfactants.

The preferred, but not only, surfactant molecule is a cationic lissome-forming surfactant N-(1-[2,3-Dioleotloxy]propyl)-N,N,N-trimethylammonium chloride (DOTAP). The structure of DOTAP itself in aqueous solution has been well characterized. Driven by the Columbic interaction, the MPS-PPV and DOTAP formed complexes in solution. Since the charge density of MPS-PPV is similar to deoxynibonucleic acid (DNA), the MPS-PPV-DOTAP particulate complex structure is similar to the DOTAP-DNA complex, which has been identified by synchrotron x-ray diffraction. Moreover, the particulates are transferable to cells, forming the basis for important cellular differentiation.

Figure 1:
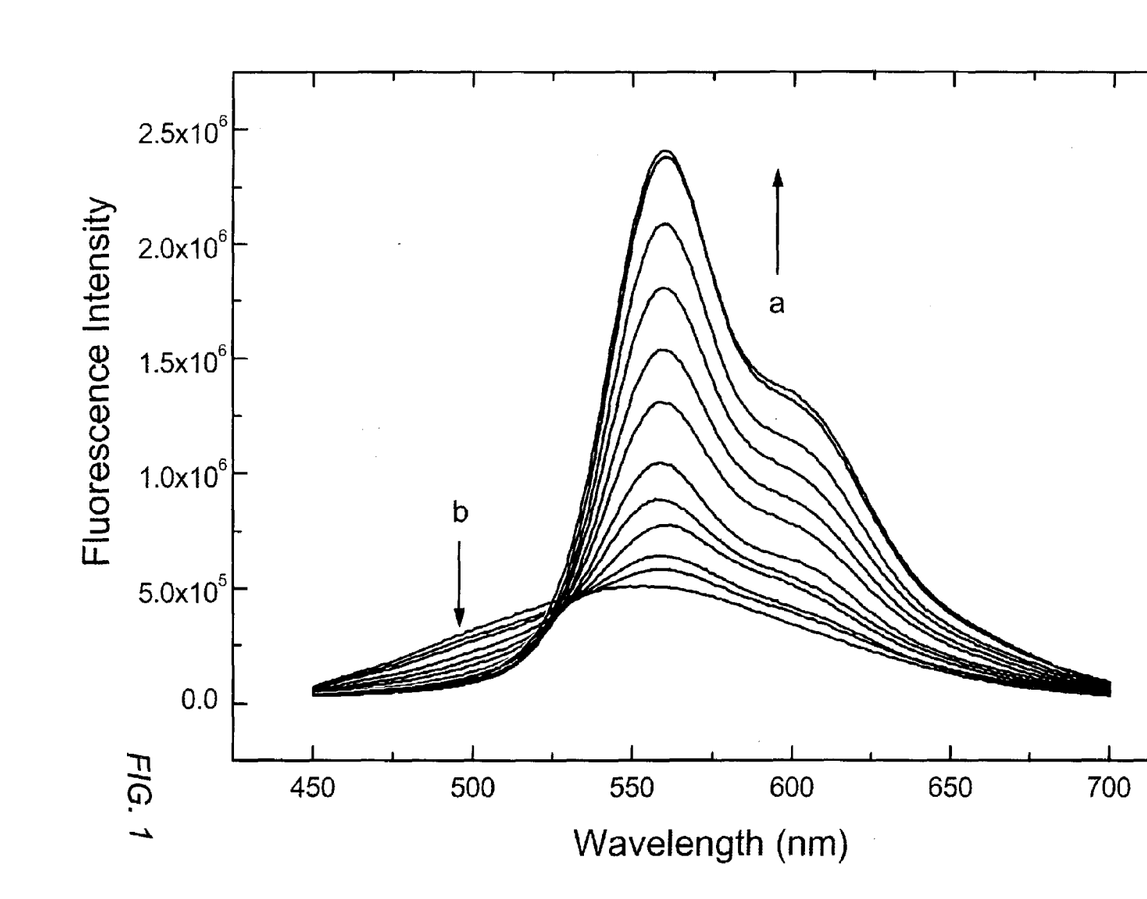
FIG. 1 is a graphical representation of the emission spectra of MPS-PPV in water.

The emission spectra of pure MPS-PPV in water are broad, structureless and strongly dependent on the excitation wavelength. However, they are changed dramatically upon the addition of DOTAP. As shown in FIG. 1, the emission intensity of MPS-PPV ($1.5 \times 10^{-5}$ M in monomer repeat units) is increased up to 5 fold and saturated as the ratio of DOTAP to MPS-PPV reaches 1:1. The emission spectra of polymer surfactant mixture are narrowed with a well-defined vibronic structure and independent of the excitation wavelength. The spectral features of the polymer surfactant mixture clearly indicate the formation of polymer-surfactant complex, and a more ordered conformation of the polymers in the complex. In contrast, the steady wavelength-dependent emission nature of pure MPS-PPV indicates chain conformational disorder and a broad distribution of coherent conjugated units. DOTAP molecules appear to extend the MPS-PPV chains, thus reducing the conformational disorder. There is a "pseudo" isosbestic point in the emission spectra of MPS-PPV as the DOTAP concentration is increased. This indicates the existence of a secondary MPS-PPV-DOTAP component (b) as the dominated complex (a)

is formed. Later experiments have shown that the decrease of the emission of component (b) is due to the formation of smaller particles toward the 15 nm range, which have a blue shifted spectroscopic response, and thus are less sensitive to 430 nm excitation.

Figure 2A:
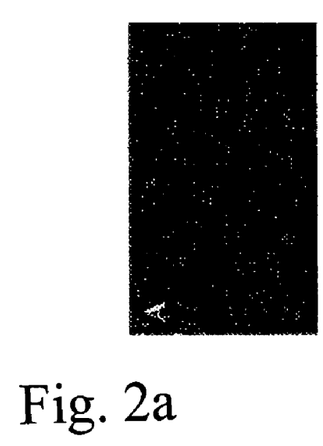
FIG. 2a is a fluorescence microscopic image of MPS-PPV DOTAP complex (1:1 ratio) using 100× oil immerse objective.

More striking results come from fluorescence microscopy of the polymer-surfactant complex (1:1 mole ratio). After filtration with a 100 nanometer filter, the $5\times10^{-5}$ M complex solution is perfectly clear and suitable for spectroscopic studies. However, when spread on a glass substrate (microscope slide) with a cover glass, incubated for 10 minutes at room temperature and observed under a 100× oil immerse objective, the polymer-surfactant complex consists of bright, uniform and well-defined nano-sized particles (FIG. 2A). The particles also exhibit strong fluorescence in the solid state with similar emission features. In contrast, MPS-PPV itself is not fluorescent in the solid state. The particle size was measured using dynamic light scattering methods. In was found that the complex solution contains particles with an average size of ~35 nm, but with a range of from about 15 to about 50 nm. As a comparison, the measured particle size in pure MPS-PPV solution is about 9 nm with a broad gaussian distribution; while pure DOTAP solution contains particles (presumably lipid bilayer assemblies) with a mean diameter of 57 nm, consistent with the literature value. The sizes of the polymer and complex particles are consistent with the results from fluorescence correlation spectroscopic experiments.

Figure 2B:
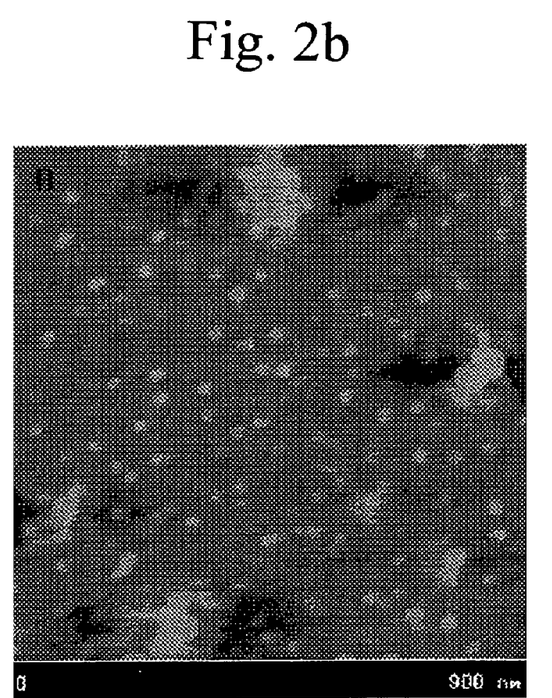
FIG. 2b is an AFM height image of MPS-PPV nanoparticles.
Figure 2C:
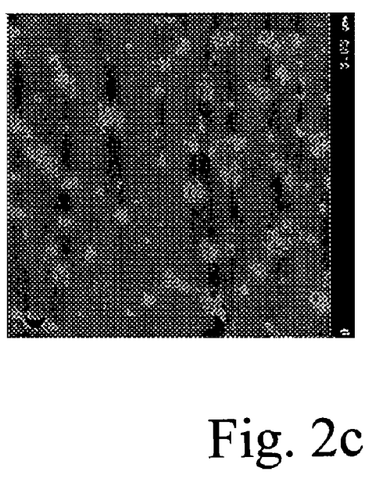
FIG. 2c is an AFM height imaging of MPS-PPV nanoparticles obtained after re-dispersion from the solid phase.

AFM (Atomic Force Microscopy) studies provide direct evidence for the formation of MPS-PPV nano-particles. A dispersed solution of $5\times10^{-5}$ M MPS-PPV-DOTAP complex (1:1 ratio) solution was filtered (100 nm pore) and spread on a freshly cleaved mica surface. In one experiment, the loaded surface was allowed to dry at room temperature to reach the solid state, while in another experiment; the solution was incubated for one hour to allow the particles to settle on the surface. All samples were examined by AFM using a fluid cell filled with pure water. The fluorescence from the particles could be observed by the microscopy, in which AFM measurements were carried out. As shown in FIG. 2B, uniform particles with an average size of about 30 nm were observed in all samples. Scattered large particles especially in dried samples were also present (FIG. 2C). Since the solution was filtered with a 100 nm filter prior to the AFM measurements, these large particles (>100 nm) must form via aggregation of 30 nm particles during the settlement or the evaporation of solvent. However, after being collected and re-dispersed in water, followed by probe-sonicated for 1 minute, the AFM image again revealed uniformly distributed nano-particles with the same average size of about 30 nm. Although MPS-PPV-DOTAP particles tend to aggregate when the solvent is evaporated, nanoscale particles still serve as basic units in the solid phase and can be re-dispersed in the solution upon sonication.

Figure 3:
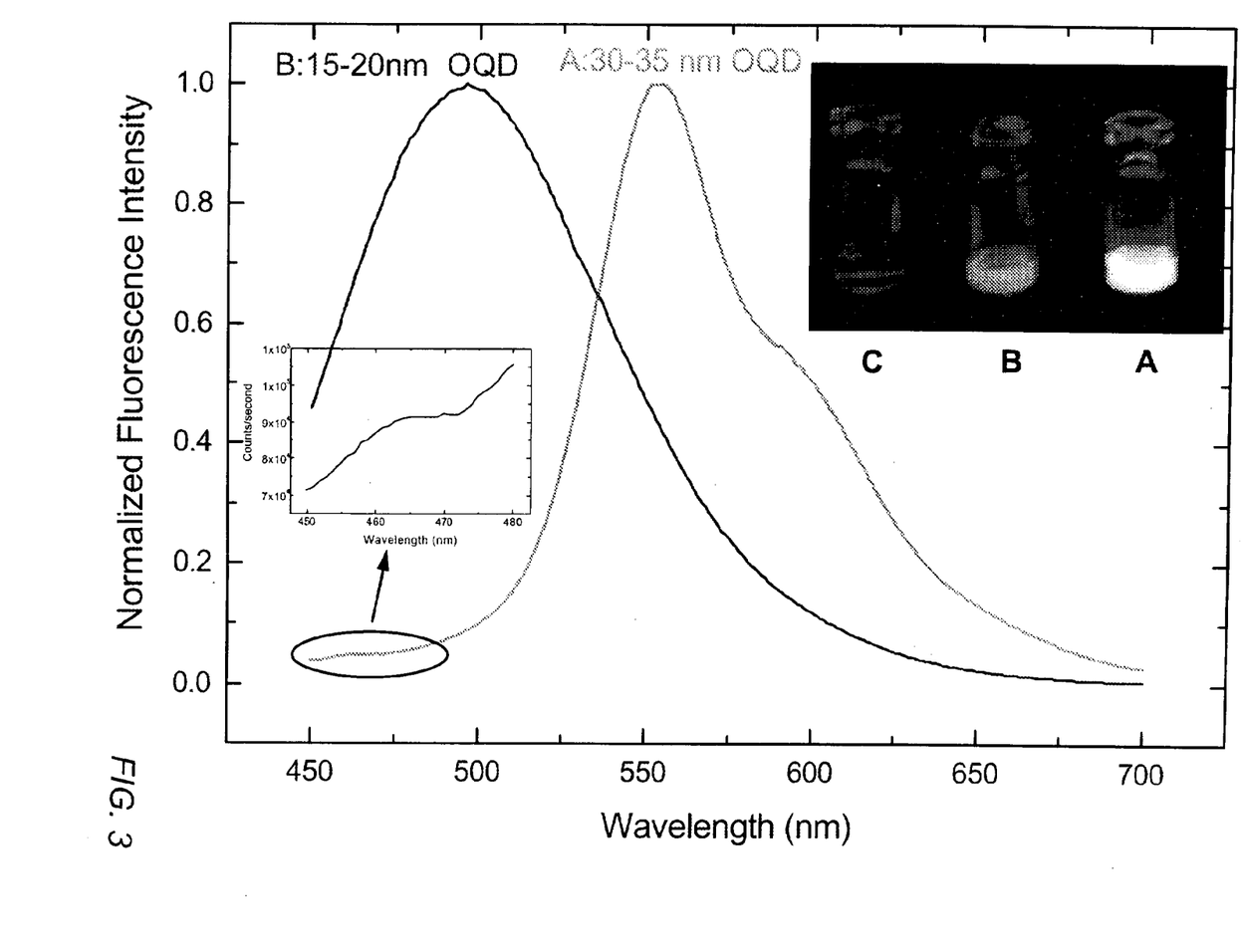
FIG. 3 are graphical representations of normalized emission spectra and the picture of MPS—PPV of intensity versus wavelength for (insert A nanoparticle 30—35 nm (yellow); insert B nanoparticle 15—20 nm (blue) and insert C nanoparticle DOTAP.

Since the spectra in FIG. 1 indicated the possibility of a second complex component in the polymer-surfactant mixture, the solution emission was examined using a shorter excitation wavelength (400 nm). As shown in FIG. 3 (inset A), the solution does container a very low concentration of species emitting at 465 nm. It is believed that the size of this species is smaller than the main particles based on the blue shift of emission spectrum. Indeed, by passing the MPS-PPV-DOTAP complex solution (1:1 ratio) through a 20 nm filter (Anodisc 47, Whatman), a solution containing the species with strong blue fluorescence was obtained, see FIG. 3, inset B. Further addition of DOTAP molecules to the smaller particle solution did not change its fluorescence. When dried, this species is also fluorescent in the solid state with a similar spectrum. Dynamic light scattering experiments indicated that the solution contains particles with an average size of 20 nm. The size of the particles is also confirmed by the fact that a 15 nm filter (Nuclepore Polycarbonate Membrane, Whatman) can effectively block almost all the particles. Since pure MPS-PPV in solution can pass through both 20 and 15 nm filters without significant loss or changes in the optical properties, it was concluded that the different fluorescence responses from two size of the particles is due to the interaction of DOTAP and MPS-PPV. Given the fact that MPS-PPV has been purified by passing through a 100 kD dialysis film, which eliminates lower molecular weight polymers, the possibility that smaller particles came from the interaction of surfactant with oligomers was excluded. Comparing to 30–35 nm MPS-PPV-DOTAP particles with bright yellow fluorescence, the obtained 15–20 nm particles share the same chemical components yet exhibit distinctive blue emission, see FIG. 3, inset B.

Figure 4:
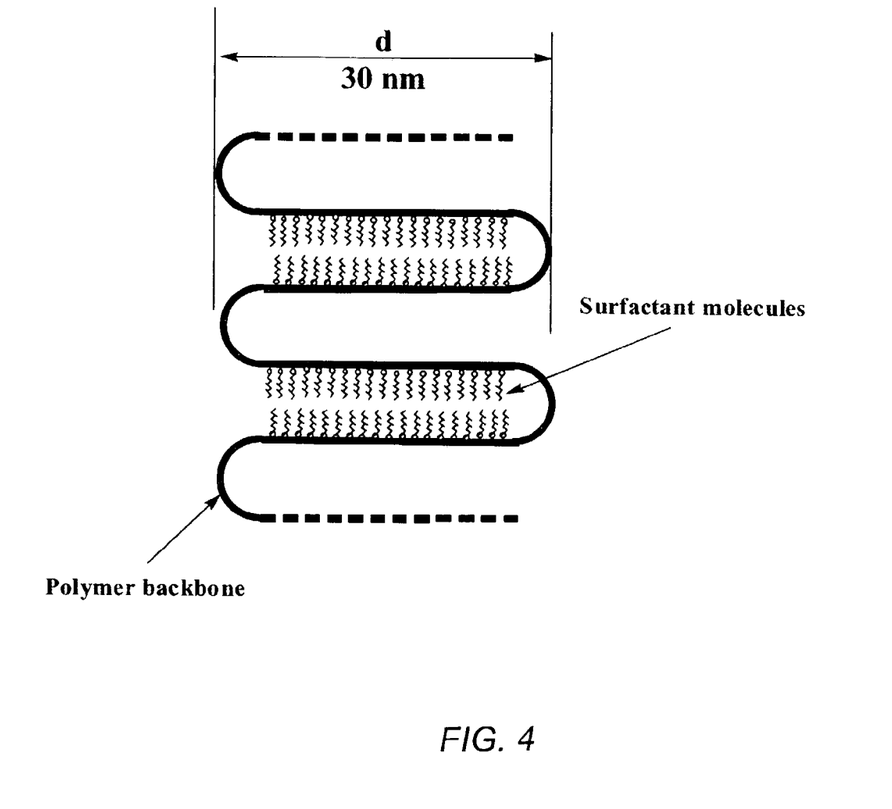
FIG. 4 is a schematic representation for the ladder-on-string model complex.

The formation of the complexes of the present invention is believed to be driven by a combination of Coulombic attraction between the ionic units ($SO^{3-}$) of the polymer and the charged surfactant head groups [$^+N(CH_3)_3R$], and by favorable entropy changes resulting from the release of interfacial water molecules upon complex formation. Once DOTAP molecules attach to the polymer backbone, the local concentration of DOTAP near the polymer chain will be much higher than that in the bulk solution. Since DOTAP tends to form bilayer structures in aqueous solution, it is reasonable to propose, without being limited, a "ladder-on-string" model to describe the structures of these organic quantum dots, see FIG. 4. The observed nano-sized particles are believed to be an assembly of linked "ladder" (subunits) that form due to the interaction between the DOTAP and polymer and the self-assembly of DOTAP. In each subunit area, the polymer chain is stretched and ordered, thus providing increased fluorescence yield compared to the bulk polymer. It is the subunit which determines the optical properties of the observed particles. The spectral features of the particles suggest that they have uniform subunits. The length of the subunit is determined by the globe energy of the complex, and the maximum length of subunit could be the diameter of the particles. It is believed that smaller subunits can be packed more densely, thus making smaller particles such as 20 nm particles, and exhibiting different optical properties, such as a blue shifted emission due to shorter coherent length. The "Ladder-on-string" structure also explains why the nano-particles are fluorescent in the solid state due to the fact that the polymer can still be considered dissolved in surfactant matrix in the solid state.

Figure 5:
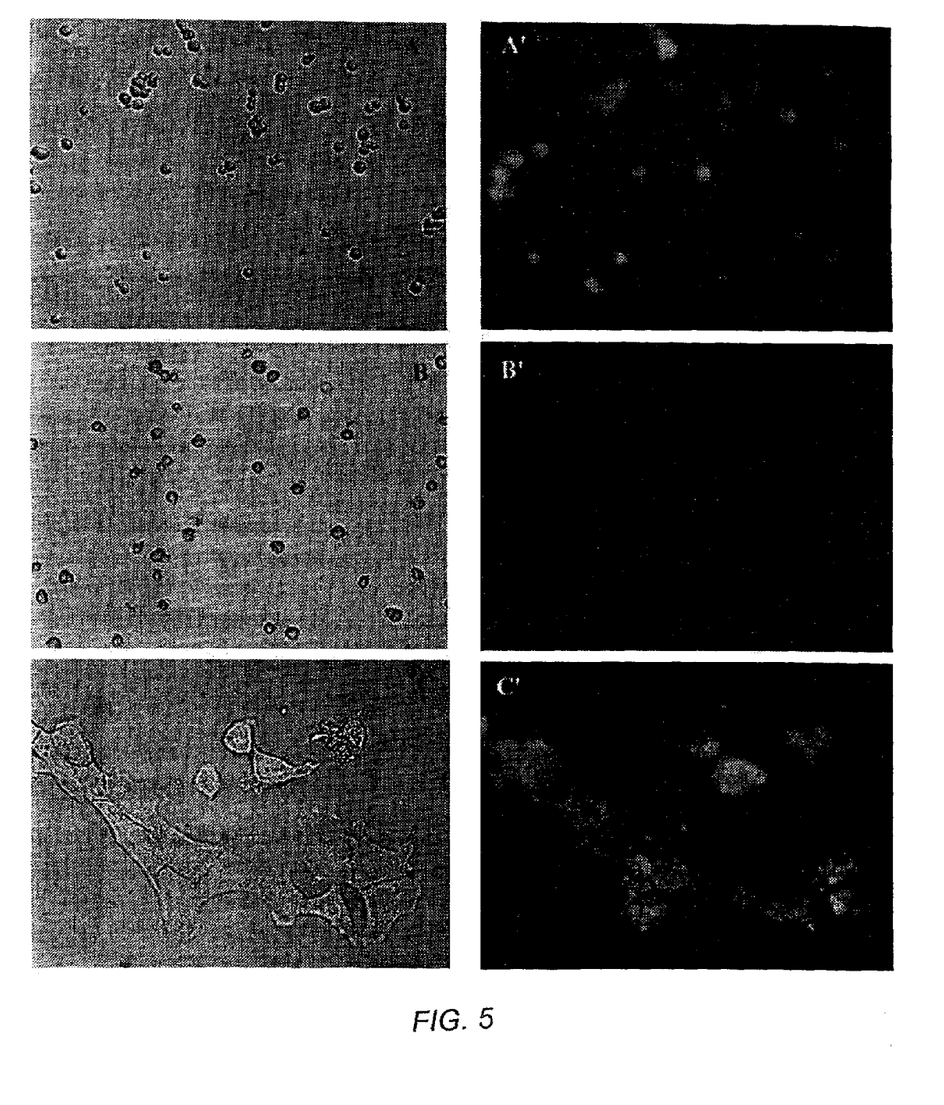
FIG. 5 is a phase contrast (left) and fluorescence (right) image of cells after incubating with $2 \times 10^{-8}$ M complex in their medium for three hours. A and A': typsinized SKOV-3 cancer cells in PBS buffer using a 20× objective, B and B': typsinized HUVEC cells in PBS buffer using a 20× objective, C and C' attached SKOV-3 cancer cells using a 60× oil immerse objective. CAOV-3 cancer cells show similar images.

The cancer cells chosen for experimentation were adenocarcinoma ovary cells SK-OV-3 and CA-OV-3 (ATCC). The closest control cells from commercial cultured cell-lines are primary human umbilical vein endothelial cells (HUVEC, Cascade Biologics, Inc.). As expected, both ovarian cancer cells respond very differently to the inventive material compared to HUVEC cells. The control cells from commercial cultured cell-lines were primary human umbilical vein endothelial cells (HUVEC, Cascade Biologics, Inc.). As expected both ovarian cancer cells respond very differently to the inventive material compared to HUVEC cells. After the cells were incubated with the medium containing $2\times10^{-8}$ M of the inventive particulate complexes for three hours, there were no noticeable changes in morphology or cell viability indicating that inventive materials are not toxic for the cells. As shown in FIG. 5, after typsinized and washed with PBS buffer, both SK-OV-3 and CA-OV-3 cancer cells show strong fluorescent signals and can be visualized with fluorescence microscopy, see FIG. 5A. However, HUVEC cells uptake fewer particles and remain dark even after 20 hours of incubation, see FIG. 5B'. Using higher magnification objectives, cancer cells can be visualized in situ as shown in FIG. 5C' while HUVEC cells show only weak fluorescence, which is insufficient for imaging. Uptaking the inventive particulates by cells via lipid transfect mechanism can be discounted because it has been reported that DNA-DOTAP complex can be effectively transfected to HUVEC cells. In addition, lipid transfection would not be cancer cell specific. It is also unlikely that cancer cells exhibit specific receptors against the inventive material, thus, uptaking might be due to the particle size being smaller enough for cancerous cells but too big for "normal" cells.

The invention relates to a new class of conjugated polymer based nano-particles and methods of making and using same by harnessing the interaction of conjugated polymer and surfactant and the self-assembly of surfactant. Given the fact that ovarian cancer cells might be found in the body fluid at an early stage, this method provides an early diagnostic method for ovarian cancer.

While particular embodiments of the present invention have been shown and described, it will be appreciated by those skilled in the art that changes, modifications and improvements may be made, for example in the processing of the materials or in the electrode and/or cell design without departing from the true spirit and scope of the invention.

The embodiments of the invention in which an exclusive property or privilege is claimed are defined as follows:

1. A particulate fluorescent conjugated polymer-surfactant composition comprising: an ionic conjugated polymer having fluorescent properties complexed with an oppositely charged surfactant of N-[1-(2,3-dioleoyloxy) propyl]-N,N,N-trimethylammonium chloride (DOTAP) in particle form, wherein the complex is characterized by at least one enhanced photophysical property and the particles have an average diameter less than about (50) nm.

2. A particulate fluorescent conjugated polymer-surfactant composition according to claim 1, wherein the enhanced photophysical property is selected from an increased fluorescence quantum efficiency, an excitation wavelength independent fluorescence emission spectrum, a narrowed and red-shifted absorption spectrum, or fluorescence decay kinetics described by single exponential decay.

3. A particulate fluorescent conjugated polymer-surfactant composition according to claim 1, wherein the surfactant forms a bilayer structure with said polymer.

4. A particulate fluorescent conjugated polymer-surfactant composition of claim 1, wherein the surfactant comprises liposome surfactant molecules.

5. A particulate fluorescent conjugated polymer-surfactant composition according to claim 1, wherein the polymer comprises at least one fluorescent ionic conjugated polymer selected from substituted and unsubstituted forms of poly(phenylene vinylene), poly(silyl-phenylene vinylene), poly(thienylene vinylene), poly(naphthalene vinylene), poly(quinoline vinylene), poly(pyridine vinylene), poly(thiophene), or derivatives thereof.

6. A particulate fluorescent conjugated polymer-surfactant composition according to claim 1, wherein the polymer is a substituted, water soluble polyanionic derivative of (polyphenylene, vinylene).

7. A particulate fluorescent conjugated polymer-surfactant composition according to claim 6, wherein the polymer is a poly(2,5-methoxy propyloxysulfonate phenylene vinylene).

8. A particulate fluorescent conjugated polymer-surfactant composition according to claim 1, wherein the ratio of surfactant molecules per monomer repeat unit of polymer is at least 0.5:1.

9. A particulate fluorescent conjugated polymer-surfactant composition according to claim 1, wherein the ratio of surfactant molecules per monomer repeat unit of polymer is not greater than about 2:1.

10. A particulate fluorescent conjugated polymer-surfactant composition according to claim 1, wherein the particles have average diameters in the range of from about 15 to less than about 50 nanometers.

11. A particulate fluorescent conjugated polymer-surfactant composition comprising a polyanionic derivative of polyphenylene vinylene having fluorescent properties complexed with a cationic liposome surfactant of N-[1-(2,3-dioleoyloxy)propyl]-N,N,N-trimethylammonium chloride (DOTAP) in particle form, wherein the complex is characterized by at least one enhanced photophysical property and the particles have an average diameter less than about (50) nm.

12. A method of preparing a particulate fluorescent conjugated polymer-surfactant composition having average diameters of less than about 50 nanometers comprising: providing a solution comprising an ionic conjugated polymer having fluorescent properties in polar solvent; combining an effective amount of oppositely charged sonicated surfactant of N-[1-(2,3-dioleoyloxy)propyl]-N,N,N-trimethylammonium chloride (DOTAP) in particle form capable of forming a bilayer structure with the polymer solution to form polymer-surfactant complex particulates wherein said particulates exhibit at least one enhanced photophysical property compared to the neat polymer and have average diameters of less than about 50 nanometers.

13. The method of claim 12, wherein the surfactant comprises liposome surfactant molecules.

14. The method of claim 12, wherein the polymer comprises at least one fluorescent ionic conjugated polymer selected from substituted and unsubstituted forms of poly(phenylene vinylene), poly(silyl-phenylene vinylene), poly(thienylene vinylene), poly(naphthalene vinylene), poly(quinoline vinylene), poly(pyridine vinylene), poly(thiophene), or derivatives thereof.

15. The method of claim 12, wherein the polymer is a substituted, water soluble polyanionic derivative of poly(phenylene vinylene).

16. The method of claim 12, wherein the polymer is a poly(2,5-methoxy propyloxysulfonate phenylene vinylene).

17. The method of claim 12, wherein the particulates have average diameters in the range of from about 15 to less than about 50 nanometers.

18. A method of controlling the fluorescence spectrum emission of a particulate fluorescent conjugated polymer-surfactant composition having average diameters of less than about 50 nanometers comprising: providing a solution comprising an ionic conjugated polymer having fluorescent properties in polar solvent; combining an effective amount of oppositely charged sonicated surfactant of N-[1-(2,3-dioleoyloxy)propyl]-N,N,N-trimethylammonium chloride (DOTAP) capable of forming a bilayer structure with the polymer solution to form polymer-surfactant complex particulates wherein said particulates exhibit at least one enhanced photophysical property compared to the neat polymer, and varying the average particle diameter within the range of from about 15 to less than about 50 nm to alter the fluorescence at a variety of wavelengths of light.

19. A particulate fluorescent conjugated polymer surfactant composition comprising:

an ionic conjugated polymer having fluorescent properties and a similar charge density to nucleic acids complexed with an oppositely charged surfactant of N-[1(2,3-dioleoyloxy)propyl]-N,N,N-trimethylammonium chloride (DOTAP) bindable to nucleic acids, the complex having an enhanced ability to enter living ovarian cancer cells relative to the individual components.

20. A particulate fluorescent conjugated polymer surfactant composition according to claim 19, wherein the polymer comprises at least one fluorescent ionic conjugated polymer selected from substituted and unsubstituted forms of poly(phenylene vinylene), poly(silyl-phenylene vinylene), poly(thienylene vinylene), poly(naphthalene vinylene), poly(quinoline vinylene), poly(pyridine vinylene), poly(thiophene), or derivatives thereof.

21. A particulate fluorescent conjugated polymer surfactant composition according to claim 20, wherein the polymer is a poly(2,5-methoxy propyloxysulfonate phenylene vinylene).

22. A particulate fluorescent conjugated polymer surfactant composition according to claim 19, wherein a nucleic acid is deoxyribonucleic acid.

23. A particulate fluorescent conjugated polymer surfactant composition according to claim 19, wherein the ionic conjugated polymer has a similar charge density to ribonucleic acid.

24. A particulate fluorescent conjugated polymer surfactant composition according to claim 19, wherein the complex has at least one enhanced photophysical property.

25. A method of detecting the presence of ovarian cancer cells in a cell sample comprising providing polymer-surfactant complex particulates formed from an ionic conjugated polymer having fluorescent properties in polar solvent and an effective amount of oppositely charged sonicated surfactant of N-[1-(2,3-dioleoyloxy)propyl]-N,N,N-trimethylammonium chloride (DOTAP) capable of forming a bilayer structure with the ionic conjugated polymer, wherein said particulates exhibit at least one enhanced photophysical property compared to the neat polymer, combining the cell sample with the polymer-surfactant complex particulates and varying the average particulate diameter within the range of from about 15 to about 50 nm to alter the fluorescence between blue and yellow to a plurality of cells, whereby the cancer cells, if present in the cell sample, absorb a greater concentration of fluorescent particles than non-cancer cells.

26. The method of claim 25, wherein the polymer is a poly(2,5-methoxy propyloxysulfonate phenylene vinylene).

* * * * *